(12) United States Patent
Valcore, Jr. et al.

(10) Patent No.: US 8,901,935 B2
(45) Date of Patent: Dec. 2, 2014

(54) METHODS AND APPARATUS FOR DETECTING THE CONFINEMENT STATE OF PLASMA IN A PLASMA PROCESSING SYSTEM

(75) Inventors: John C. Valcore, Jr., Mt. View, CA (US); James Rogers, Los Gatos, CA (US)

(73) Assignee: Lam Research Corporation, Fremont, CA (US)

( * ) Notice: Subject to any disclaimer, the term of this patent is extended or adjusted under 35 U.S.C. 154(b) by 370 days.

(21) Appl. No.: 12/907,859

(22) Filed: Oct. 19, 2010

(65) Prior Publication Data

US 2011/0115492 A1 May 19, 2011

Related U.S. Application Data

(60) Provisional application No. 61/303,628, filed on Feb. 11, 2010, provisional application No. 61/262,886, filed on Nov. 19, 2009.

(51) Int. Cl.
*G01N 27/62* (2006.01)

(52) U.S. Cl.
CPC ..................................... *G01N 27/62* (2013.01)
USPC ............................ 324/464; 361/234; 438/712

(58) Field of Classification Search
CPC . G01N 27/464; G01N 27/536; G01N 27/713; G01N 30/64; G01N 2030/642; H01J 37/32935; G01R 31/1227; G01R 31/1254; G01R 31/1272; G01R 19/00; G01R 19/0092; C23C 16/505
USPC .......... 324/464, 536, 713; 156/627.1; 216/60; 361/234; 427/533; 438/7; 700/121
See application file for complete search history.

(56) References Cited

U.S. PATENT DOCUMENTS 4,222,838 A * 9/1980 Bhagat et al. ............ 204/192.32
5,474,648 A * 12/1995 Patrick et al. .................... 438/10

(Continued)

FOREIGN PATENT DOCUMENTS

JP 2001-127045 5/2001
JP 2004-3355921 11/2004

(Continued)

OTHER PUBLICATIONS

"Non Final Office Action", U.S. Appl. No. 12/950,710, Mailing Date: Oct. 12, 2012.

(Continued)

*Primary Examiner* — Huy Q Phan
*Assistant Examiner* — Giovanni Astacio-Oquendo
(74) *Attorney, Agent, or Firm* — Martine Penilla Group, LLP

(57) ABSTRACT

Methods and systems for detecting a change in the state of plasma confinement within a capacitively coupled RF driven plasma processing chamber are disclosed. In one or more embodiments, the plasma unconfinement detection methods employ an analog or digital circuit that can actively poll the RF voltage at the powered electrode in the form of an Electrostatic Chuck (ESC) as well as the open loop response of the power supply (PSU) responsible for chucking a wafer to ESC. The circuit provides a means detecting both a change in RF voltage delivered to the ESC as well as a change in the open loop response of the PSU. By simultaneously monitoring these electrical signals, the disclosed algorithm can detect when plasma changes from a confined to an unconfined state.

17 Claims, 4 Drawing Sheets

(56) References Cited

U.S. PATENT DOCUMENTS

| | | | |
|---|---|---|---|
| 5,737,177 A | | 4/1998 | Mett et al. |
| 5,764,471 A | | 6/1998 | Burkhart |
| 5,801,386 A | * | 9/1998 | Todorov et al. ............... 250/397 |
| 5,812,361 A | | 9/1998 | Jones et al. |
| 5,894,400 A | | 4/1999 | Graven et al. |
| 5,933,314 A | * | 8/1999 | Lambson et al. ............. 361/234 |
| 5,980,767 A | * | 11/1999 | Koshimizu et al. ............ 216/60 |
| 6,198,616 B1 | | 3/2001 | Dahimene et al. |
| 6,522,121 B2 | | 2/2003 | Coumou |
| 6,535,785 B2 | | 3/2003 | Johnson et al. |
| 6,677,246 B2 | | 1/2004 | Scanlan et al. |
| 7,169,625 B2 | | 1/2007 | Davis |
| 7,359,177 B2 | | 4/2008 | Yang et al. |
| 7,505,879 B2 | | 3/2009 | Tomoyasu et al. |
| 7,728,602 B2 | | 6/2010 | Valcore et al. |
| 7,768,269 B2 | * | 8/2010 | Pipitone et al. ............... 324/536 |
| 2003/0082835 A1 | | 5/2003 | McChesney et al. |
| 2003/0103793 A1 | | 6/2003 | Murakoshi et al. |
| 2003/0169553 A1 | * | 9/2003 | Brown et al. ................. 361/234 |
| 2004/0028837 A1 | | 2/2004 | Fink |
| 2004/0060660 A1 | | 4/2004 | Klimecky et al. |
| 2004/0087047 A1 | | 5/2004 | Jaiswal et al. |
| 2004/0135590 A1 | * | 7/2004 | Quon ............................ 324/713 |
| 2005/0252884 A1 | | 11/2005 | Lam et al. |
| 2006/0256499 A1 | * | 11/2006 | Yang et al. .................... 361/234 |
| 2007/0065594 A1 | | 3/2007 | Chiang et al. |
| 2009/0151871 A1 | | 6/2009 | Pease et al. |
| 2009/0272402 A1 | * | 11/2009 | Kim et al. ....................... 134/1.2 |
| 2010/0033195 A1 | * | 2/2010 | Booth et al. ................... 324/663 |
| 2010/0096361 A1 | * | 4/2010 | Fischer et al. ................. 216/61 |
| 2010/0279028 A1 | * | 11/2010 | Dine ............................. 427/569 |

FOREIGN PATENT DOCUMENTS

| | | |
|---|---|---|
| KR | 10-2005-0088438 | 9/2005 |
| KR | 10-2005-0089995 | 9/2005 |
| KR | 10-2007-0031915 | 3/2007 |
| WO | WO-2008-002938 | 1/2008 |

OTHER PUBLICATIONS

U.S. Appl. No. 61/262,886, filed Nov. 19, 2009.
U.S. Appl. No. 61/303,628, filed Feb. 11, 2010.
U.S. Appl. No. 12/950,710, filed Nov. 19, 2010.
U.S. Appl. No. 12/962,524, filed Dec. 7, 2010.
Non Final Office Action, U.S. Appl. No. 12/962,524, Mailing Date: Apr. 12, 2012.
International Search Report, PCT Application Number: PCT/US2011/063422, Mailing Date: Mar. 28, 2012.
Written Opinion, PCT Application Number: PCT/US2011/063422, Mailing Date: Mar. 28, 2012.
"International Preliminary Report on Patentability", PCT Application No. PCT/US2010/057478, Mailing Date: May 31, 2012.
"International Search Report", PCT Application Number: PCT/US2010/057450, Mailing Date: Jul. 18, 2011.
"Written Opinion", PCT Application Number: PCT/US2010/057450, Mailing Date: Jul. 18, 2011.
"International Search Report", PCT Application Number: PCT/US2010/057478, Mailing Date: Jul. 26, 2011.
"Written Opinion", PCT Application No. PCT/US2010/057478, Mailing Date: Jul. 26, 2011.
Final Office Action, U.S. Appl. No. 12/950,710, Mailing Date: Feb. 6, 2013.
Non Final Office Action, U.S. Appl. No. 12/950,710, Mailing Date: Jun. 13, 2013.
Notice of Allowance and Fees Due, U.S. Appl. No. 12/962,524, Mailing Date: Apr. 3, 2013.

* cited by examiner

US 8,901,935 B2

METHODS AND APPARATUS FOR DETECTING THE CONFINEMENT STATE OF PLASMA IN A PLASMA PROCESSING SYSTEM

PRIORITY CLAIM

This application claims priority under 35 USC. 119(e) to a commonly-owned provisional patent application entitled "BIAS COMPENSATION APPARATUS AND METHODS THEREFOR", U.S. application Ser. No. 61/303,628, filed on Feb. 10, 2010 by John Valcore, Jr. and a commonly-owned provisional patent application entitled "METHOD AND DEVICE FOR COMPENSATING WAFER BIAS IN A RF DRIVEN PLASMA CHAMBER", U.S. application Ser. No. 61/262,886, filed on Nov. 19, 2009 by John Valcore, Jr., both of which are incorporated herein by reference.

BACKGROUND OF THE INVENTION

In the manufacture of semiconductor products, substrates (e.g., semiconductor wafers) are processed by successively depositing, etching, and polishing various layers to create semiconductor devices. Within the semiconductor industry, it is common practice to utilize the benefits of a RF (Radio Frequency) driven plasma to dry etch material from a substrate. During plasma etch processes, it is paramount that the stability and uniformity of the plasma is controlled in order to improve process efficiency and yield for the substrate under process. This can be accomplished through a variety of methods, one of which is to control the plasma formation through the use of mechanical and electrical elements within the plasma chamber to confine the plasma to the process region of interest. These arrangements are well-known in the art and will not be elaborated further here.

While plasma confinement is a well understood practice; there is a need to detect when confined plasma changes to an unconfined state within a process chamber. Unconfined plasma can cause particle contamination and plasma non-uniformities, leading to degradation in the yield of the substrate under process and/or damage to the plasma processing system. A current scheme for detecting a change in plasma confinement employs a Si Carbide pin that is attached to the outer ring of the electro-static chuck (ESC) and in direct contact with the plasma. U.S. Pat. No. 5,737,177, issued Apr. 7, 1998, discloses one such scheme. While this instrument provides a relatively reliable means of detecting a change in plasma confinement by providing a DC (direct current) measurement of plasma sheath potential, it is a consumable part that must be replaced frequently and can induce plasma non-uniformities at higher RF powers and can result in particle contamination issues. Another scheme for detecting a change in plasma confinement is through the use of an OES technique (Optical Emission Spectroscopy) technique. However, it has been found that monitoring OES signals is an unduly complex and oftentimes unreliable method of detecting plasma unconfinement events.

Therefore, alternate methods and arrangements for detecting unconfined plasma events in a plasma processing system are desired.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In one or more embodiments, methods and apparatus for detecting a change in the state of plasma confinement within a capacitively coupled, RF driven plasma processing chamber are disclosed. In one or more embodiments, the plasma unconfinement detection methods employ an analog and/or digital circuit that can actively poll the RF voltage at the powered electrode in the form of an Electrostatic Chuck (ESC) as well as the open loop response of the bias power supply (PSU) responsible for chucking a wafer to the ESC. Embodiments of the invention facilitate detection of both a change in the RF voltage delivered to the ESC as well as a change in the open loop response of the PSU. By simultaneously monitoring these electrical signals, the disclosed techniques can detect when plasma changes from a confined to an unconfined state.

In one or more embodiments of the invention, the rate of change (derivative) and optionally the magnitude of the change of both the RF voltage delivered to the ESC (RF_VDT_ESC) and the open loop response (OLR_DC_BIAS) of the DC bias ESC power supply are examined. In the regime where the rate of change of the RF_VDT_ESC is positive and rate of change of the OLR_DC_BIAS is negative, an abnormal condition alert is triggered. If the magnitude of the changes is above a certain threshold that has previously been empirically determined to be indicative of a plasma unconfinement event, a plasma unconfinement condition is deemed to have occurred and an unconfinement alert signal is generated, in one or more embodiments.

To further elaborate, it has been discovered that when the plasma changes from a confined to unconfined state, the computed ESC Bias value using RF voltage parameters was inversely proportional to the true plasma sheath voltage. Upon further review of the system, it has been discovered that the open loop response of the ESC Power Supply Unit (PSU) DC/DC brick responsible for driving the reference voltage for the ESC poles oscillates when the plasma changes from a confined to unconfined state, a reflection of the increased plasma sheath voltage.

Figure 1:
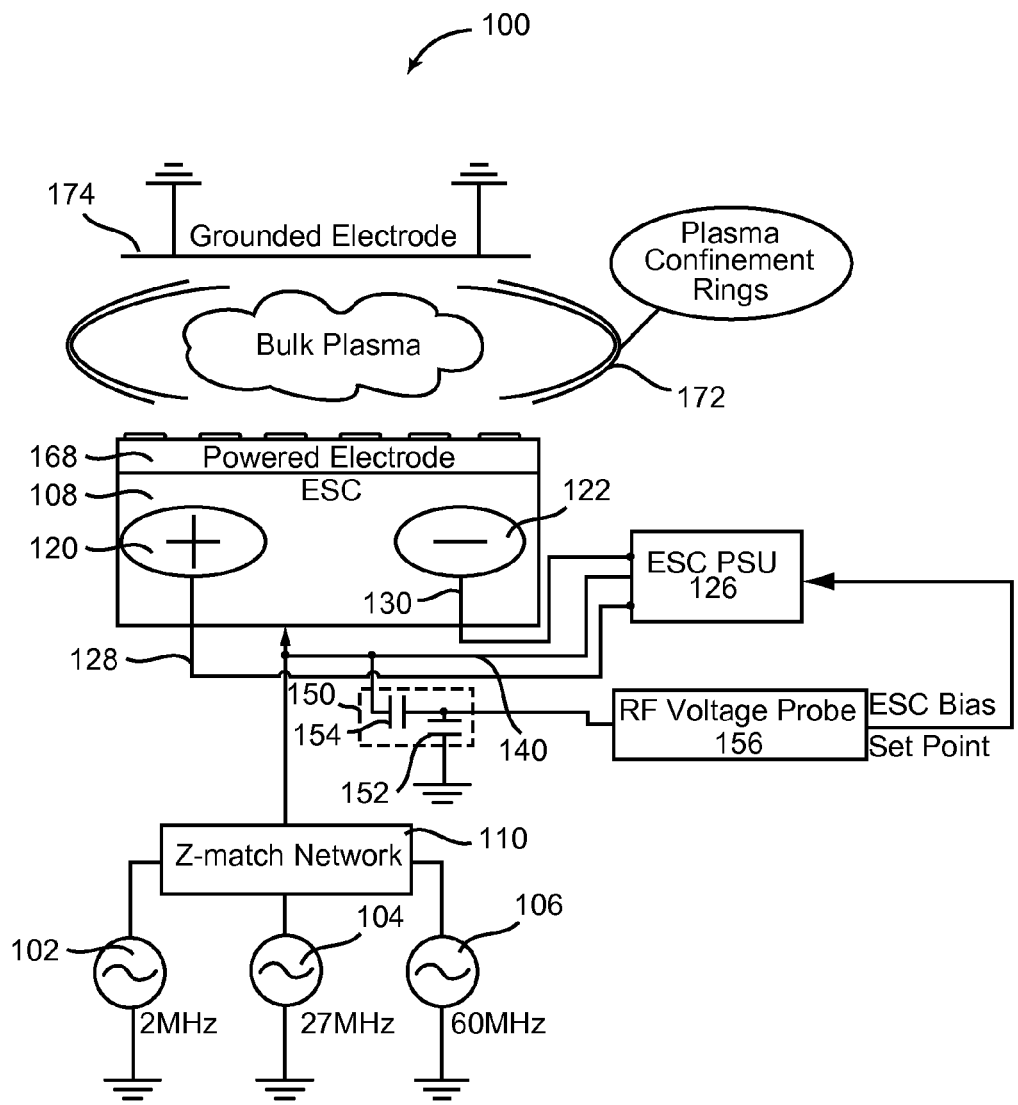
FIG. 1 is an example system configuration for producing confined multi-frequency capacitive RF plasma, in accordance with an embodiment of the present invention.

FIG. 1 is an example system configuration for generating confined multi-frequency capacitive RF plasma, where the powered electrode is a bipolar ESC. Plasma is also confined by a set of circular quartz rings, controlling the flow of gas and thus controlling the space within which the plasma exists.

Plasma processing system 100 is a multi-frequency capacitively-coupled plasma processing system in which three RF power supplies 102, 104, and 106 deliver RF voltages to an ESC chuck 108 via a match network 110. In the example of FIG. 1, 3 RF frequencies (2 MHz, 27 MHz, and 60 MHz) are employed although any number and range of frequencies may be employed.

ESC 108 is a bipolar ESC in that there are two poles: a positive pole 120 and a negative pole 122. An ESC PSU 126 supplies the clamping voltages to poles 120 and 122 via conductors 128 and 130 respectively. A center tap 140 drives the DC potential of ESC 108 to bias the DC potential of the ESC 108.

Capacitor divider network 150 (comprising capacitors 152 and 154) and RF voltage probe 156 are employed to derive an ESC bias set point signal, which is input as a feedback signal to ESC PSU 126 to control the ESC bias provided to ESC 108. Further details regarding RF voltage probe 156 are disclosed in a commonly-owned provisional patent application entitled "BIAS COMPENSATION APPARATUS AND METHODS THEREFOR", U.S. application Ser. No. 61/303,628, filed on Feb. 10, 2010 by John Valcore, Jr. and a commonly-owned provisional patent application entitled "METHOD AND DEVICE FOR COMPENSATING WAFER BIAS IN A RF DRIVEN PLASMA CHAMBER", U.S. application Ser. No. 61/262,886, filed on Nov. 19, 2009 by John Valcore, Jr., both of which are incorporated herein by reference.

As will be discussed later herein, the inherent delay in this feedback loop results in the presence of an momentary response that is detectable at center tap 140 when a plasma unconfinement event occurs. This momentary, essentially open-loop response is brief and occurs before the feedback signal from RF voltage probe 156 can compensate. By monitoring the rate of change and optionally the magnitude of change of this momentary, open loop response of ESC PSU 126 (OLR_DC_BIAS), one of the two metrics indicative of a plasma unconfinement event may be detected. The other metric of the two metrics indicative of a plasma unconfinement event is the rate of change and optionally magnitude of the RF voltage delivered to ESC chuck 108, as discussed earlier.

For completeness in the discussion of FIG. 1, a wafer is typically disposed on a powered electrode 168 which is in turn disposed above ESC chuck 108. During processing, a bulk plasma 170 is formed above the wafer, and is confined by a set of confinement rings 172 as well by upper grounded electrode 174.

Figure 2:
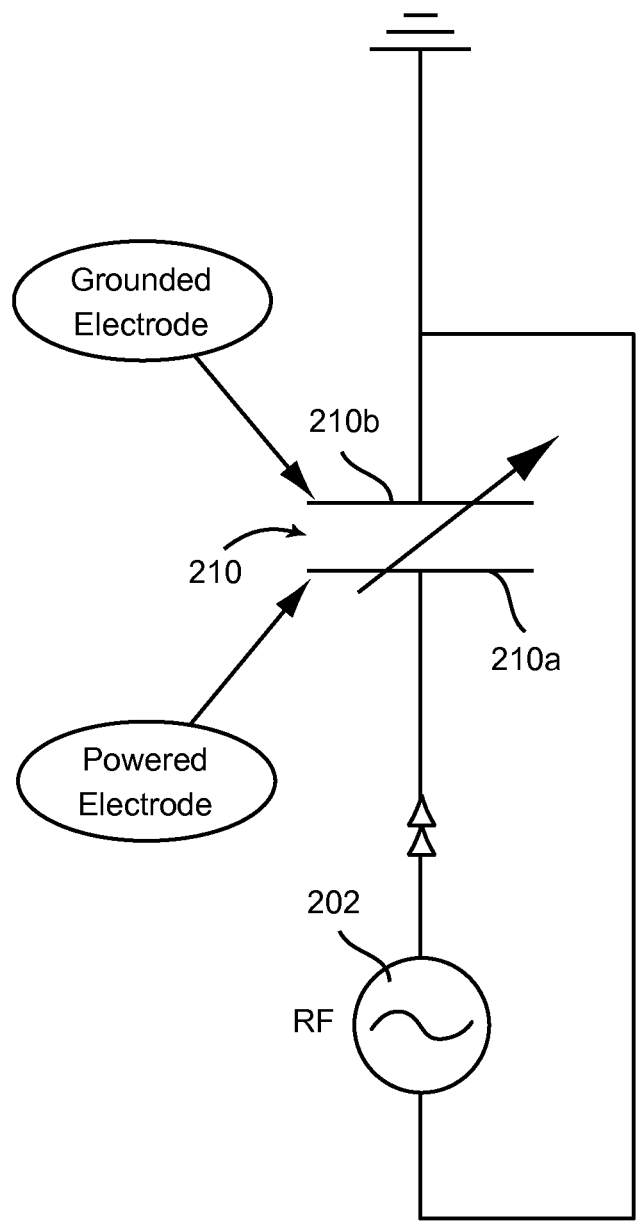
FIG. 2 illustrates, in accordance with an embodiment of the present invention, a simplified circuit of the RF components of FIG. 1.

It has been discovered that when the plasma transitions from a confined state to an unconfined state, the rate of change and the magnitude of the RF voltage delivered to the ESC chuck are increased. FIG. 2 illustrates a simplified circuit of the RF components of FIG. 1. The impedance matching network 110 and independent RF sources (102, 104, and 106) of FIG. 1 are consolidated into a single RF source 202 in FIG. 2. Powered electrode 168, grounded electrode 174, and plasma confinement rings 172 of FIG. 1 are represented by a simple variable capacitor 210 with plate 210a representing powered electrode 168 and plate 210b representing grounded electrode 174.

Given that the capacitance of the chamber is a direct function of the surface area of the electrodes, and the confinement rings control the effective surface area that is utilized in the chamber, a first order approximation of the equivalent electrical circuit for the capacitive chamber in FIG. 1 can be reduced to FIG. 2 by ignoring inductive and resistance circuit components. This simplified circuit can be used to illustrate the correlation between the plasma impedance, the magnitude of the RF voltage delivered to the ESC chuck and the state of plasma confinement.

Given that RF power is a function of voltage, and plasma impedance is a function of voltage as well as of the capacitance of the chamber, if RF power is constant and the capacitance of the chamber increases as the plasma moves from a confined to unconfined state thereby increases the grounded area, then the RF voltage delivered to the ESC chuck must decrease. This correlation of RF voltage to grounded area for a constant RF power provides a fundamental element in detecting a state change in plasma confinement.

To further elaborate, capacitance is defined by:

$$C = K*E*A/D \qquad \text{Eq. 1}$$

Where C is the capacitance; K is the dielectric constant of the electrodes; E is the permittivity of free space; A is the area of the electrodes; and D is the distance between the electrodes.

In the confined state, the confinement rings control the capacitance by constraining the plasma, thus limiting the surface area that the current flows between the electrodes. Unconfined plasma causes an increase in the area A. When A increases, capacitance C also increases per Eq. 1.

For an ideal capacitor, impedance is defined by:

$$Z = SQRT(R^2 + (1/(2*Pi*f*C)^2)) \qquad \text{Eq. 2}$$

Wherein R=0; Pi is a mathematical constant; f is the frequency of the RF source; C is the capacitance. If f is constant, it can be seen from Eq. 2 that Z is inversely proportional to C.

Power delivery is governed by Eq. 3 below.

$$P = I*V*\cos(\text{theta}) \qquad \text{Eq. 3}$$

Where P is power; I is current, V is voltage; and theta is the phase between V and I.

RF power delivered is a function of impedance.

$$Z = V/I \qquad \text{Eq. 4}$$

Wherein Z is the impedance, V is voltage, and I is current. When R=0, Z can be simplified to be 1/(2*Pi*f*C) (see Eq. 2 above).

Given that Z is approximately 1/(2*Pi*f*C), it follows then from Eq. 4, that $$1/(2*Pi*f*C) = V/I \qquad \text{Eq. 5}$$

Since C=K*E*A/D (see Eq. 1), when A increases due to an unconfinement plasma event, C increases and Z decreases.

Further, since P=I*V*cos(theta) (see Eq. 3), if P is constant and theta is constant, if C increases, V decreases and I increases.

Thus, as can be seen in from FIG. 2 and the discussion that accompanies FIG. 2, the transition from a confined plasma state to an unconfined plasma state is accompanied by an increase (positive derivative) in the RF voltage delivered to the ESC. The detection of this increase in the RF voltage delivered to the ESC represents one condition in the proposed unconfinement plasma detection scheme. If desired, a magnitude threshold or magnitude change threshold may be established to reduce false positives.

Figure 3:
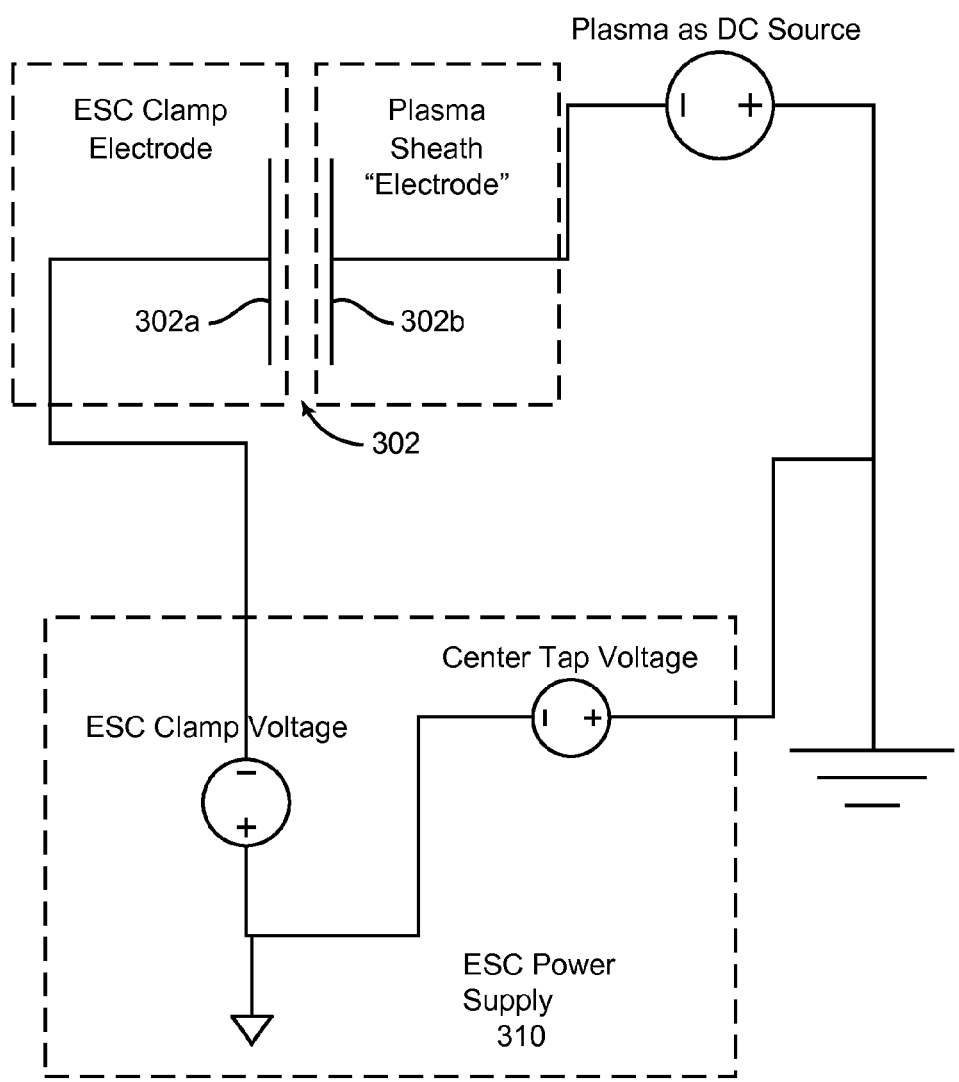
FIG. 3 illustrates, in accordance with an embodiment of the present invention, the correlation between the ESC pole voltage and the state of plasma confinement.

In addition to the correlation of the RF voltage supplied to the ESC to plasma confinement, it has been discovered that there is another fundamental correlation between the ESC pole voltage and plasma confinement. FIG. 3 illustrates the correlation between ESC pole voltage(s) and the state of plasma confinement. In this simplified DC equivalent circuit of FIG. 3, a parallel plate capacitor 302 comprising plate 302a (representing the ESC clamp electrode) and plate 302b (representing the wafer) is presented. Parallel plate capacitor 302 is formed between the ESC pole and the plasma sheath, where the ceramic and wafer form the dielectric between the two plates.

The ESC pole is driven by a DC power supply 310 and the sheath voltage is a function of plasma acting as a DC source. Given that the ratio of powered electrode voltage to ground electrode voltage is equal to the ratio of ground electrode area to powered electrode area (ratio holds true for both DC and RF), as the area of the ground electrode increases due to the occurrence of an unconfined plasma event and the powered electrode area remains constant, the sheath voltage increases.

In FIG. 3, the DC voltage at the ESC pole is a function of voltage supplied by the ESC PSU 310 as well as the charge on the opposite pole and the capacitance formed by the two poles. As the sheath voltage increases as the plasma changes from a confined to unconfined state and the capacitance remains constant between the poles, the ESC pole will be charged by the sheath voltage. This charging effect can be seen in the impulse response of the ESC PSU 310 as the plasma goes unconfined.

In particular, the center tap DC voltage supply will oscillate as a function of the load change induced by the charging of the ESC pole voltage. The center tap DC supply is used to maintain the reference voltage for the ESC clamp voltage supply for the purpose of providing a consistent clamp force on the wafer regardless of the plasma sheath potential. The momentary open loop response of the ESC PSU 310 (present at the center tap) provides the second metric used in detecting the state of plasma confinement (and correspondingly the state of plasma unconfinement).

Using both the change in RF voltage delivered to the ESC and the change in ESC PSU open loop response in response to the plasma changing from a confined to unconfined state provides the necessary parameters for detecting the state change of plasma confinement.

Figure 4:
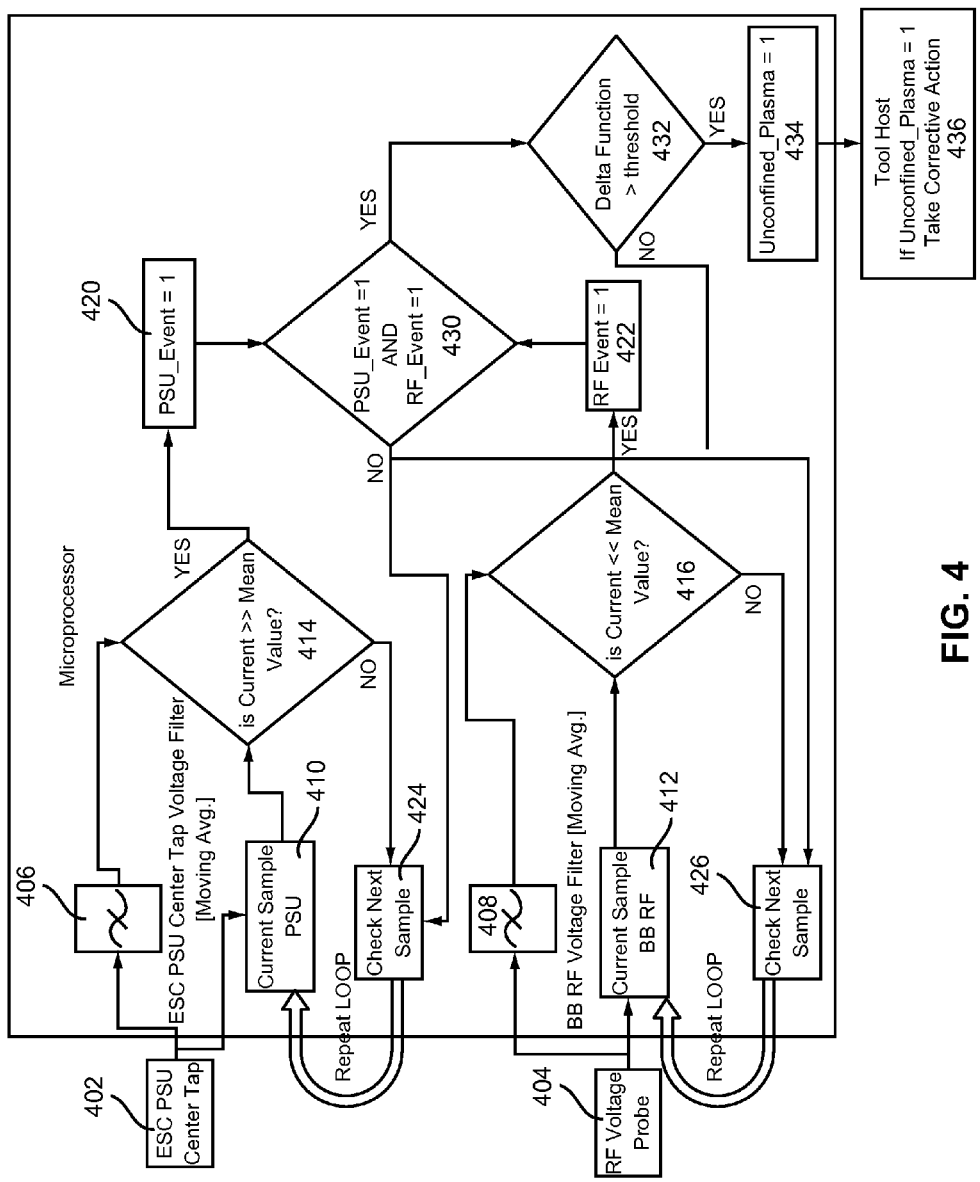
FIG. 4 is a flow diagram of an example algorithm implementing the plasma unconfinement detection technique, in accordance with an embodiment of the present invention.

FIG. 4 is a flow diagram of an example algorithm implemented within a microprocessor and/or via code, with the input parameters being the DC voltage measured at the ESC PSU center tap (402) and a RF voltage probe parameter (404). The RF voltage probe parameter 404 can be a singular or a composite signal representative of the RF voltage at the ESC. For the sake of simplicity, the RF Voltage parameter is labeled Broadband RF (BB RF) signal, and will be referred to as BB RF from here forward.

The BB RF signal and the ESC PSU Center Tap voltage are fed through independent low pass filters (408 and 406 respectively). FIG. 4 refers to a first order low pass filter known as a simple moving average. However, it should be understood that any other suitable filter, whether analog or digital, may also be employed. The output of each respective filter is then compared to the current sample of each respective signal (410 and 412). The comparison is shown in blocks 414 and 416.

If there is a sufficient positive magnitude change (dv/dt>>0) in the ESC PSU Center Tap voltage (414) then an event flag is set, labeled 'PSU_Event=1' in block 420 of FIG. 4. In similar fashion, if the BB RF signal has a sufficient negative magnitude (dv/dt<<0) (block 416) then an event flag is set, labeled 'RF_Event=1' (block 422). If either event flag fails to be set to the equivalent digital "on" state, then the detection loop will continue to poll and compare the next available sample for each respective signal (block 424 and 426).

If both event flags are toggled on (block 430), a delta function is computed. This delta function computes the magnitude of the RF BB derivate with respect to the magnitude of the ESC PSU Center Tap derivate. If the derivates are of sufficient magnitude relative one another (block 432), then a 'Unconfined_Plasma=1' event flag (434) is sent to the Tool host (436), responsible for controlling the plasma chamber so that corrective action can be taken, such as changing RF delivered power, changing the pressure or gas flow to the chamber, or adjusting the confinement ring position, or the like.

Alternatively, it is possible to monitor the electrical center tap current to the ESC baseplate, rather than or in addition to the center tap voltage. The sudden current required to charge the capacitor shown in FIG. 2 during an unconfinement event would also be another suitable indicator of a potential uncontrolled processing condition event.

In one or more embodiments, the plasma unconfinement detection scheme may be implemented within the analog domain using analog low pass filters and comparators and/or within the digital domain using a DSP. FPGA/CPLD, or microprocessor. In one or more embodiments, the RF Voltage probe can be located anywhere along the transmission line between the impedance matching network and the powered electrode, as seen in FIG. 1. In one or more embodiments, the ESC PSU center tap voltage can be measured anywhere between the ESC and the ESC PSU internal circuit. In one or more embodiments, a high impedance voltage divider at the base of the ESC is employed, as seen in FIG. 1, and the ESC PSU center tap voltage at the direct output of the ESC PSU. Both of these signals may then be fed, in one or more embodiments, into a PIC 18F4523 8-bit microprocessor with an equivalent 40 MHz clock (available from Microchip Technology™, Inc. of Chandler, Ariz.).

In one or more embodiments, the time scale and direction of the transient responses may be a function of the driving RF frequencies, as well as the amount of power associated with each RF frequency. In one or more embodiments, RF signals with more power tend to dominate, and the responses at these frequencies may be more pronounced, which render detection more reliable. These are general observations that may be incorporated into a detection strategy, in one or more embodiments.

As can be appreciated from the foregoing, embodiments of the invention enable the detection of an abnormal plasma condition (of which plasma unconfinement is an example) without requiring the use of an intrusive, in-situ monitoring instrument. In so doing, issues regarding plasma-induced wear, contamination, and replacement/cleaning associated with such in-situ monitoring instruments are eliminated. By monitoring both the change in the RF voltage delivered to the ESC and the change in the open loop response of the ESC PSU and optionally employing thresholding to reduce false positives, embodiments of the invention provide a robust technique for detecting abnormal plasma conditions, thereby enabling the tool host to provide timely corrective measures or to shut down the tool to avoid further damage.

Having disclosed exemplary embodiments and the best mode, modifications and variations may be made to the disclosed embodiments while remaining within the subject and spirit of the invention as defined by the following claims.

What is claimed is:

1. A method for detecting plasma unconfinement in a plasma processing chamber, said plasma processing chamber having an electrostatic (ESC) chuck, comprising:
   providing an RF voltage to said ESC chuck;
   providing a ESC power supply unit configured to provide a DC bias voltage to said ESC chuck, said ESC power supply unit having a center tap coupled to receive said RF voltage;
   simultaneously monitoring said RF voltage and said center tap for changes indicative of a plasma unconfinement condition wherein said monitoring includes detecting a positive derivative of a change in said RF voltage; and providing a signal to indicate a presence of said plasma unconfinement condition if said plasma unconfinement condition is detected by said monitoring.

2. The method of claim 1 wherein said RF voltage is a broadband RF voltage comprising at least two RF frequencies.

3. The method of claim 1 wherein said monitoring further includes ascertaining whether a magnitude of said change exceeds a predefined threshold.

4. The method of claim 1 wherein said monitoring includes detecting said change in an open-loop DC response on said center tap.

5. The method of claim 4 wherein said monitoring further includes ascertaining whether a magnitude of said change exceeds a predefined threshold.

6. The method of claim 1 wherein said monitoring includes detecting said change in an open-loop DC response on said center tap.

7. The method of claim 6 wherein said open-loop DC response represents an open-loop DC voltage.

8. The method of claim 6 wherein said open-loop DC response represents an open-loop DC current.

9. The method of claim 1 wherein said monitoring includes detecting a rate of change in said RF voltage and detecting a rate of said change in an open-loop DC response on said center tap.

10. The method of claim 1 wherein said signal is employed as a feedback signal to automatically initiate corrective action in response to a detection of said plasma unconfinement condition.

11. An arrangement for detecting plasma unconfinement in a plasma processing chamber, said plasma processing chamber having an electrostatic (ESC) chuck, said ESC chuck being configured to receive an RF voltage, comprising:

a ESC power supply unit configured to provide a DC bias voltage to said ESC chuck, said ESC power supply unit having a center tap coupled to receive said RF voltage; and means for analyzing said RF voltage and an open-loop DC response on said center tap for changes indicative of a plasma unconfinement condition wherein said means for analyzing said RF includes means for detecting a positive derivative of a change in said RF voltage.

12. The arrangement of claim 11 wherein said RF voltage is a broadband RF voltage comprising at least two RF frequencies.

13. The arrangement of claim 11 wherein said means for analyzing is further configured to ascertain whether a magnitude of said change in said RF voltage exceeds a predefined threshold.

14. The arrangement of claim 11 wherein said means for analyzing is configured to at least detect said change in an open-loop DC response on said center tap.

15. The arrangement of claim 11 wherein said means for analyzing is further configured to ascertain whether a magnitude of said change in said open-loop DC response exceeds a predefined threshold.

16. The arrangement of claim 11 wherein said open-loop DC response represents an open-loop DC voltage.

17. The arrangement of claim 11 wherein said means for analyzing includes detecting a rate of said change in said RF voltage and detecting a rate of change in an open-loop DC response on said center tap.

* * * * *